(12) United States Patent
Adams et al.

(10) Patent No.: US 9,072,534 B2
(45) Date of Patent: Jul. 7, 2015

(54) NON-CAVITATION SHOCKWAVE BALLOON CATHETER SYSTEM

(75) Inventors: John M. Adams, Snohomish, WA (US); Clifton A. Alferness, Olalla, VT (US); Daniel Hawkins, Fremont, CA (US)

(73) Assignee: SHOCKWAVE MEDICAL, INC., Fremont, CA (US)

( * ) Notice: Subject to any disclaimer, the term of this patent is extended or adjusted under 35 U.S.C. 154(b) by 473 days.

(21) Appl. No.: 13/465,264

(22) Filed: May 7, 2012

(65) Prior Publication Data
US 2012/0221013 A1 Aug. 30, 2012

Related U.S. Application Data

(63) Continuation-in-part of application No. 12/482,995, filed on Jun. 11, 2009, now Pat. No. 8,956,371.

(60) Provisional application No. 61/061,170, filed on Jun. 13, 2008.

(51) Int. Cl.
*A61B 17/225* (2006.01)
*A61B 17/22* (2006.01)
*A61B 17/3207* (2006.01)

(52) U.S. Cl.
CPC ....... *A61B 17/2202* (2013.01); *A61B 17/22022* (2013.01); *A61B 17/2251* (2013.01); *A61B 17/320725* (2013.01); *A61B 2017/22024* (2013.01); *A61B 2017/22025* (2013.01)

(58) Field of Classification Search
USPC .................. 606/1–4, 15, 48, 127, 128, 159; 601/2–4
See application file for complete search history.

(56) References Cited

U.S. PATENT DOCUMENTS

| 3,413,976 | A | * | 12/1968 | Voolfovich ................ 606/128 |
| 3,785,382 | A | | 1/1974 | Schmidt-Kloiber et al. |
| 3,902,499 | A | * | 9/1975 | Shene ........................ 606/128 |
| 4,027,674 | A | | 6/1977 | Tessler et al. |
| 4,662,126 | A | | 5/1987 | Malcolm |
| 4,671,254 | A | * | 6/1987 | Fair ............................... 601/3 |

(Continued)

FOREIGN PATENT DOCUMENTS

| DE | 3038445 A1 | 5/1982 |
| EP | 0442199 A2 | 8/1991 |

(Continued)

OTHER PUBLICATIONS

International Search Report and Written Opinion received for PCT Patent Application No. PCT/US2013/039987, mailed on Sep. 23, 2013, 15 pages.

(Continued)

*Primary Examiner* — Kathleen Holwerda
(74) *Attorney, Agent, or Firm* — Morrison & Foerster LLP

(57) ABSTRACT

An angioplasty catheter includes an elongated carrier, and an angioplasty balloon about the carrier in sealed relation thereto. The balloon is arranged to receive a fluid therein that inflates the balloon. The catheter further includes a shock wave generator within the balloon that forms a rapidly expanding and collapsing bubble within the balloon to form mechanical shock waves within the balloon. The expanding bubble forms a first shock and the collapsing balloon forms a second shock wave. The shock wave generator is arranged such that the energy of the first shock wave is greater than the energy of the second shock wave.

17 Claims, 9 Drawing Sheets

(56) References Cited

U.S. PATENT DOCUMENTS

| | | | |
|---|---|---|---|
| 4,685,458 A | | 8/1987 | Leckrone |
| 4,809,682 A | * | 3/1989 | Forssmann et al. ............... 601/4 |
| 4,900,303 A | | 2/1990 | Lemelson |
| 5,009,232 A | | 4/1991 | Hassler et al. |
| 5,057,103 A | | 10/1991 | Davis |
| 5,057,106 A | | 10/1991 | Kasevich et al. |
| 5,078,717 A | | 1/1992 | Parins et al. |
| 5,103,804 A | | 4/1992 | Abele et al. |
| 5,152,767 A | * | 10/1992 | Sypal et al. ................... 606/128 |
| 5,152,768 A | | 10/1992 | Bhatta |
| 5,176,675 A | | 1/1993 | Watson et al. |
| 5,245,988 A | | 9/1993 | Einars et al. |
| 5,246,447 A | | 9/1993 | Rosen et al. |
| 5,281,231 A | | 1/1994 | Rosen et al. |
| 5,324,255 A | | 6/1994 | Passafaro et al. |
| 5,336,234 A | | 8/1994 | Vigil et al. |
| 5,368,591 A | | 11/1994 | Lennox et al. |
| 5,395,335 A | | 3/1995 | Jang |
| 5,417,208 A | | 5/1995 | Winkler |
| 5,425,735 A | | 6/1995 | Rosen et al. |
| 5,472,406 A | | 12/1995 | de la Torre et al. |
| 5,582,578 A | * | 12/1996 | Zhong et al. ...................... 601/4 |
| 5,603,731 A | | 2/1997 | Whitney |
| 5,609,606 A | | 3/1997 | O'Boyle |
| 5,662,590 A | | 9/1997 | de la Torre et al. |
| 5,931,805 A | | 8/1999 | Brisken |
| 6,007,530 A | | 12/1999 | Dornhofer et al. |
| 6,033,371 A | | 3/2000 | Torre et al. |
| 6,083,232 A | | 7/2000 | Cox |
| 6,210,408 B1 | | 4/2001 | Chandrasekaran et al. |
| 6,217,531 B1 | | 4/2001 | Reitmajer |
| 6,277,138 B1 | | 8/2001 | Levinson et al. |
| 6,287,272 B1 | | 9/2001 | Brisken et al. |
| 6,352,535 B1 | * | 3/2002 | Lewis et al. ...................... 606/45 |
| 6,367,203 B1 | | 4/2002 | Graham et al. |
| 6,371,971 B1 | | 4/2002 | Tsugita et al. |
| 6,398,792 B1 | | 6/2002 | O'Connor |
| 6,406,486 B1 | | 6/2002 | DeLa Torre et al. |
| 6,514,203 B2 | | 2/2003 | Bukshpan |
| 6,524,251 B2 | | 2/2003 | Rabiner et al. |
| 6,589,253 B1 | | 7/2003 | Cornish et al. |
| 6,607,003 B1 | | 8/2003 | Wilson |
| 6,638,246 B1 | | 10/2003 | Naimark et al. |
| 6,652,547 B2 | | 11/2003 | Rabiner et al. |
| 6,736,784 B1 | | 5/2004 | Menne et al. |
| 6,740,081 B2 | | 5/2004 | Hilal |
| 6,755,821 B1 | | 6/2004 | Fry |
| 6,989,009 B2 | | 1/2006 | Lafontaine |
| 7,241,295 B2 | | 7/2007 | Maguire |
| 7,569,032 B2 | | 8/2009 | Naimark et al. |
| 8,556,813 B2 | | 10/2013 | Cioanta et al. |
| 8,728,091 B2 | | 5/2014 | Hakala et al. |
| 8,747,416 B2 | | 6/2014 | Hakala et al. |
| 2001/0044596 A1 | | 11/2001 | Jaafar |
| 2002/0177889 A1 | | 11/2002 | Brisken et al. |
| 2003/0004434 A1 | | 1/2003 | Greco et al. |
| 2003/0176873 A1 | | 9/2003 | Chernenko et al. |
| 2003/0229370 A1 | | 12/2003 | Miller |
| 2004/0044308 A1 | | 3/2004 | Naimark et al. |
| 2004/0097996 A1 | | 5/2004 | Rabiner et al. |
| 2004/0249401 A1 | | 12/2004 | Rabiner et al. |
| 2004/0254570 A1 | | 12/2004 | Hadjicostis et al. |
| 2005/0015953 A1 | | 1/2005 | Keidar |
| 2005/0021013 A1 | | 1/2005 | Visuri et al. |
| 2005/0251131 A1 | | 11/2005 | Lesh |
| 2006/0004286 A1 | | 1/2006 | Chang et al. |
| 2006/0184076 A1 | | 8/2006 | Gill et al. |
| 2006/0190022 A1 | | 8/2006 | Beyar et al. |
| 2007/0088380 A1 | | 4/2007 | Hirszowicz et al. |
| 2007/0239082 A1 | | 10/2007 | Schultheiss et al. |
| 2007/0239253 A1 | | 10/2007 | Jagger et al. |
| 2007/0244423 A1 | | 10/2007 | Zummeris et al. |
| 2008/0097251 A1 | | 4/2008 | Babaev |
| 2008/0188913 A1 | | 8/2008 | Stone et al. |
| 2009/0041833 A1 | | 2/2009 | Bettinger et al. |
| 2009/0247945 A1 | | 10/2009 | Levit et al. |
| 2009/0254114 A1 | | 10/2009 | Hirszowicz et al. |
| 2009/0312768 A1 | | 12/2009 | Hawkins et al. |
| 2010/0016862 A1 | | 1/2010 | Hawkins et al. |
| 2010/0036294 A1 | * | 2/2010 | Mantell et al. ................... 601/4 |
| 2010/0114020 A1 | | 5/2010 | Hawkins et al. |
| 2010/0114065 A1 | | 5/2010 | Hawkins et al. |
| 2010/0121322 A1 | | 5/2010 | Swanson |
| 2010/0305565 A1 | | 12/2010 | Truckai et al. |
| 2011/0034832 A1 | | 2/2011 | Cioanta et al. |
| 2011/0118634 A1 | | 5/2011 | Golan |
| 2011/0166570 A1 | | 7/2011 | Hawkins et al. |
| 2011/0257523 A1 | | 10/2011 | Hastings et al. |
| 2011/0295227 A1 | | 12/2011 | Hawkins et al. |
| 2012/0071889 A1 | | 3/2012 | Mantell et al. |
| 2012/0095461 A1 | | 4/2012 | Herscher et al. |
| 2012/0203255 A1 | | 8/2012 | Hawkins et al. |
| 2013/0030431 A1 | | 1/2013 | Adams |
| 2013/0030447 A1 | | 1/2013 | Adams |
| 2013/0116714 A1 | | 5/2013 | Adams |
| 2013/0150874 A1 | | 6/2013 | Kassab |
| 2014/0046229 A1 | | 2/2014 | Hawkins et al. |
| 2014/0052147 A1 | | 2/2014 | Hakala et al. |
| 2014/0074111 A1 | | 3/2014 | Hakala et al. |
| 2014/0243820 A1 | | 8/2014 | Adams et al. |
| 2014/0243847 A1 | | 8/2014 | Hakala et al. |
| 2014/0288570 A1 | | 9/2014 | Adams |

FOREIGN PATENT DOCUMENTS

| | | |
|---|---|---|
| EP | 0571306 A1 | 11/1993 |
| JP | 62-275446 A | 11/1987 |
| JP | 6-125915 A | 5/1994 |
| JP | 7-47135 A | 2/1995 |
| JP | 10-99444 A | 4/1998 |
| JP | 10-513379 A | 12/1998 |
| JP | 2002-538932 A | 11/2002 |
| JP | 2004-81374 A | 3/2004 |
| JP | 2005-95410 A | 4/2005 |
| JP | 2005-515825 A | 6/2005 |
| JP | 2006-516465 A | 7/2006 |
| WO | 96/24297 A1 | 8/1996 |
| WO | 2004/069072 A2 | 8/2004 |
| WO | 2006/127158 A2 | 11/2006 |
| WO | 2007/149905 A2 | 12/2007 |
| WO | 2009/121017 A1 | 10/2009 |
| WO | 2009/152352 A2 | 12/2009 |
| WO | 014515 | 2/2010 |
| WO | 2011/143468 A2 | 11/2011 |
| WO | 2013/059735 A1 | 4/2013 |

OTHER PUBLICATIONS

International Search Report and Written Opinion received for PCT Patent Application No. PCT/US2013/048277, mailed on Oct. 2, 2013, 14 pages.

Office Action received for Japanese Patent Application No. 2011-513694, mailed on Aug. 27, 2013, 6 pages. (3 pages of English Translation and 3 pages of Official copy).

Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.

Zhong et al., "Transient Oscillation of Cavitation Bubbles Near Stone Surface During Electohydraulic Lithotripsy", Journal of Endourology, vol. 11, No. 1, Feb. 1997, pp. 55-61.

Extended European Search Report (includes Supplementary European Search Report and Search Opinion) received for European Patent Application No. 09763640.1, mailed on Oct. 10, 2013, 5 pages.

Final Office Action received for U.S. Appl. No. 13/267,383, mailed on Oct. 25, 2013, 8 pages.

International Search Report and Written Opinion received for PCT Patent Application No. PCT/US2013/059533, mailed on Nov. 7, 2013, 14 pages.

Hakala et al., Unpublished U.S. Appl. No. 14/271,276, filed May 6, 2014, titled "Shockwave Catheter System with Energy Control", 20 pages.

(56) References Cited

OTHER PUBLICATIONS

International Search Report and Written Opinion received for PCT Patent Application No. PCT/US2013/055431, mailed on Nov. 12, 2013, 9 pages.
Advisory Action received for U.S. Appl. No. 13/267,383, mailed on Jan. 6, 2014, 4 pages.
Non-Final Office Action received for U.S. Appl. No. 12/501,619, mailed on Jan. 28, 2014, 10 pages.
Non-Final Office Action received for U.S. Appl. No. 13/049,199, mailed on Feb. 4, 2014, 8 pages.
Final Office Action received for U.S. Appl. No. 12/482,995, mailed on Feb. 20, 2014, 11 pages.
Final Office Action received for U.S. Appl. No. 12/581,295, mailed on Jun. 5, 2014, 14 pages.
Non-Final Office Action received for U.S. Appl. No. 12/581,295, mailed on Mar. 10, 2014, 11 pages.
Non-Final Office Action received for U.S. Appl. No. 14/061,554, mailed on Mar. 12, 2014, 14 pages.
Notice of Allowance received for U.S. Appl. No. 14/061,554, mailed on Apr. 25, 2014, 8 pages.
Non Final Office Action received for U.S. Appl. No. 14/079,463, mailed on Mar. 4, 2014, 9 pages.
Notice of Allowance received for U.S. Appl. No. 14/079,463, mailed on Apr. 1, 2014, 5 pages.
Office Action received for Australian Patent Application No. 2009257368, issued on Apr. 28, 2014, 4 pages.
Office Action Received for Japanese Patent Application No. 2011-513694, mailed on Jun. 10, 2014, 2 pages of Official Copy only. (See Communication under 37 CFR § 1.98(a) (3)).
Adams et al., Unpublished U.S. Appl. No. 14/271,342, filed May 6, 2014, titled "Shock Wave Balloon Catheter with Multiple Shock Wave Sources", 21 pages.
Adams, John M., Unpublished U.S. Appl. No. 14/218,858, filed Mar. 18, 2014, titled "Shockwave Catheter System with Energy Control", 24 pages.
Adams, John M., Unpublished U.S. Appl. No. 14/273,063, filed May 8, 2014, titled "Shock Wave Guide Wire", 24 pages.
International Preliminary Report on Patentability received for PCT Patent Application No. PCT/US2012/063925, mailed on May 22, 2014, 12 pages.
International Search Report for International Patent Application No. PCT/US2009/047070, dated Jan. 19, 2010.
International Written Opinion received for PCT Patent Application No. PCT/US2011/047070, mailed on May 1, 2012, 5 pages.
International Preliminary Report on Patentability received for PCT Patent Application No. PCT/US2011/047070, mailed on Feb. 21, 2013, 7 pages.
International Search Report and Written Opinion received for PCT Patent Application No. PCT/US2013/031805 mailed on May 20, 2013, 13 pages.
International Search Report and Written Opinion received for PCT Patent Application No. PCT/US2012/023172, mailed on Sep. 28, 2012, 7 pages.
Adams et al., U.S. Appl. No. 13/534,658, filed Jun. 27, 2012, titled "Shock Wave Balloon Catheter with Multiple Shock Wave Sources".
Adams et al., U.S. Appl. No. 13/777,807, filed Feb. 26, 2013, titled "Shock Wave Catheter System with ARC Preconditioning".
Hakala et al., U.S. Appl. No. 13/615,107, filed Sep. 13, 2012, titled "Shockwave Catheter System with Energy Control".
Hakala et al., U.S. Appl. No. 13/831,543, filed Mar. 14, 2013, titled "Low Profile Electrodes for an Angioplasty Shock Wave Catheter", 52 pages.
Non Final Office Action received for U.S. Appl. No. 12/482,995, mailed on Jul. 12, 2013, 11 pages.
International Preliminary Report on Patentability received for PCT Patent Application No. PCT/US2012/023172, mailed on Aug. 15, 2013, 6 pages.
Office Action received for Australian Patent Application No. 2009257368, issued on Jul. 31, 2013, 4 pages.
Non Final Office Action received for U.S. Appl. No. 12/482,995, mailed on Aug. 13, 2014, 10 pages.
Advisory Action Received for U.S. Appl. No. 12/581,295, mailed on Jul. 3, 2014, 3 pages.
Final Office Action received for U.S. Appl. No. 13/049,199 mailed on Aug. 11, 2014, 8 pages.
Notice of Allowance received for U.S. Appl. No. 13/831,543, mailed on Oct. 8, 2014, 14 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Notice of Acceptance Received for Australian Patent Application No. 2009257368, mailed on Aug. 28, 2014, 2 pages.
Cleveland et al., "The Physics of Shock Wave Lithotripsy", Extracorporeal Shock Wave Lithotripsy Part IV, Chapter 38, 2012, pp. 317-332.
Connors et al., "Renal Nerves Mediate Changes in Contralateral Renal Blood Flow after Extracorporeal Shockwave Lithotripsy", Nephron Physiol, vol. 95, 2003, pp. 67-75.
Doug Hakala, "Unpublished U.S. Appl. No. 14/515,130, filed Oct. 15, 2014, titled "Low Profile Electrodes for an Angioplasty Shock Wave Catheter"".
Gambihler et al., "Permeabilization of the Plasma Membrane of L1210 Mouse Leukemia Cells Using Lithotripter Shock Waves", The Journal of Membrane Biology, vol. 141, 1994, pp. 267-275.
Grassi, et al. "Novel Antihypertensive Therapies: Renal Sympathetic Nerve Ablation and Carotid Baroreceptor Stimulation", Curr Hypertens Rep vol. 14, 2012, pp. 567-572.
Kodama et al., "Shock wave-mediated molecular delivery into cells", Biochimica et Biophysica Acta vol. 1542, 2002, pp. 186-194.
Lauer et al., "Shock wave permeabilization as a new gene transfer method", Gene Therapy vol. 4, 1997, pp. 710-715.
Non-Final Office Action received for U.S. Appl. No. 13/646,570, mailed on Oct. 29, 2014, 10 pages.
Non-Final Office Action received for U.S. Appl. No. 13/646,583, mailed on Oct. 31, 2014, 8 pages.
Written Opinon received for PCT Patent Application No. PCT/US2009/047070, mailed on Jan. 19, 2010, 5 pages.
International Preliminary Report on Patentability received for PCT Patent Application No. PCT/US2009/047070, mailed on Dec. 23, 2010, 7 pages.
Decision to Grant received for Japanese Patent Application No. 2011-513694, mailed on Oct. 7, 2014, 3 pages of official copy only (See Communication under 37 CFR § 1.98(a) (3)).
Advisory Action Received for U.S. Appl. No. 12/482,995, mailed on Jun. 2, 2014, 3 pages.
Advisory Action Received for U.S. Appl. No. 12/482,995, mailed on Sep. 29, 2011, 2 pages.
Notice of Allowance received for U.S. Appl. No. 12/482,995, mailed on Dec. 24, 2014, 6 pages.
Non-Final Office Action received for U.S. Appl. No. 12/581,295, mailed on Jan. 15, 2015, 14 pages.
Advisory Action Received for U.S. Appl. No. 13/049,199, mailed on Jun. 7, 2012, 3 pages.
Notice of Allowance received for U.S. Appl. No. 13/049,199, mailed on Dec. 15, 2014, 7 pages.
Non-Final Office Action received for U.S. Appl. No. 13/267,383, mailed on Feb. 25, 2015, 9 pages.
Final Office Action received for U.S. Appl. No. 13/646,570, mailed on Dec. 23, 2014, 10 pages.
Notice of Allowance received for U.S. Appl. No. 14/271,276, mailed on Feb. 25, 2015, 8 pages.
Final Office Action received for U.S. Appl. No. 14/271,342 mailed on Feb. 27, 2015, 7 pages.
International Written Opinion received for PCT Patent Application No. PCT/US2012/023172, mailed on Sep. 28, 2012, 4 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987 issued on Nov. 20, 2014, 11 pages.
International Preliminary Report on Patentability received for PCT Patent Application No. PCT/US2013/048277 mailed on Jan. 8, 2015, 9 pages.
International Preliminary Report on Patentability received for PCT Patent Application No. PCT/US2013/055431, mailed on Feb. 26, 2015, 7 pages.

* cited by examiner

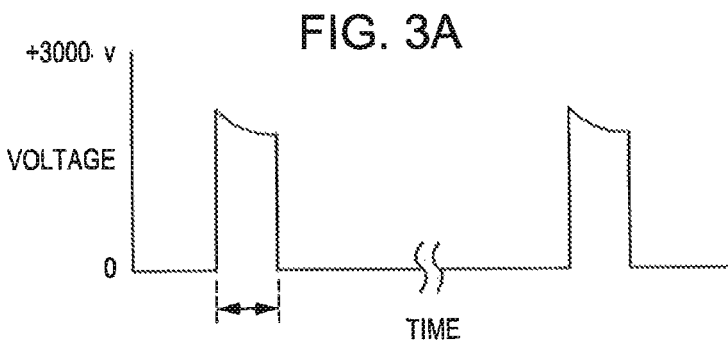
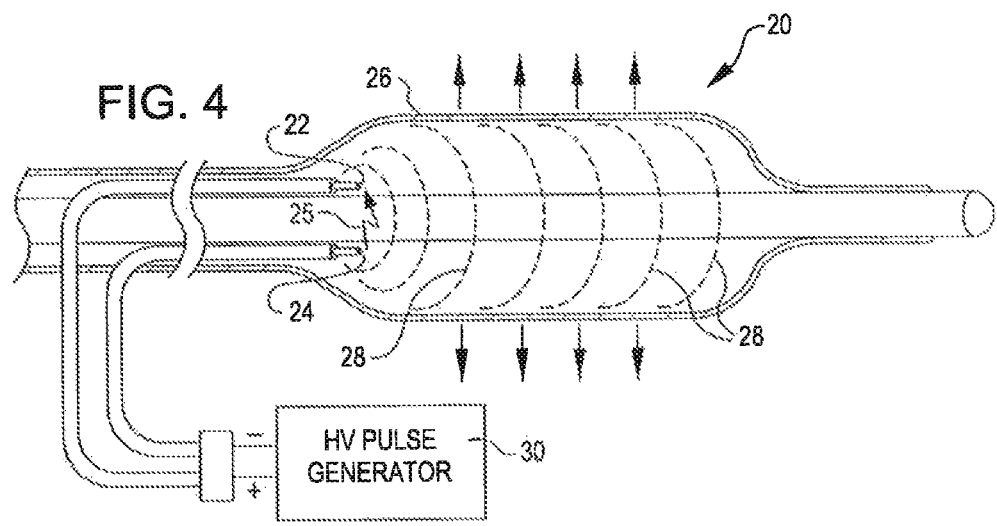
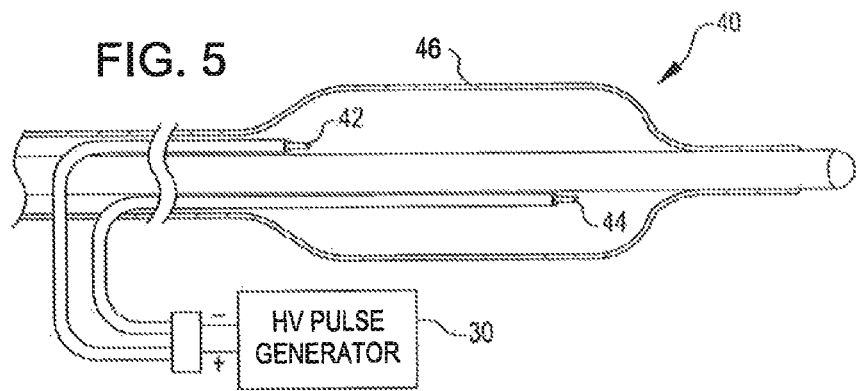

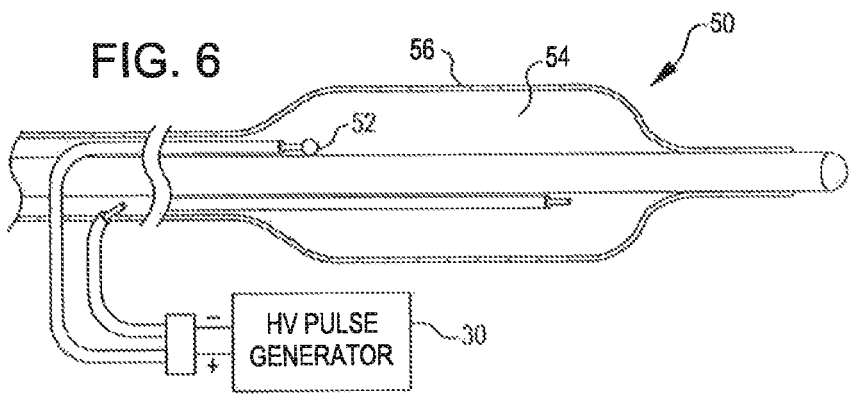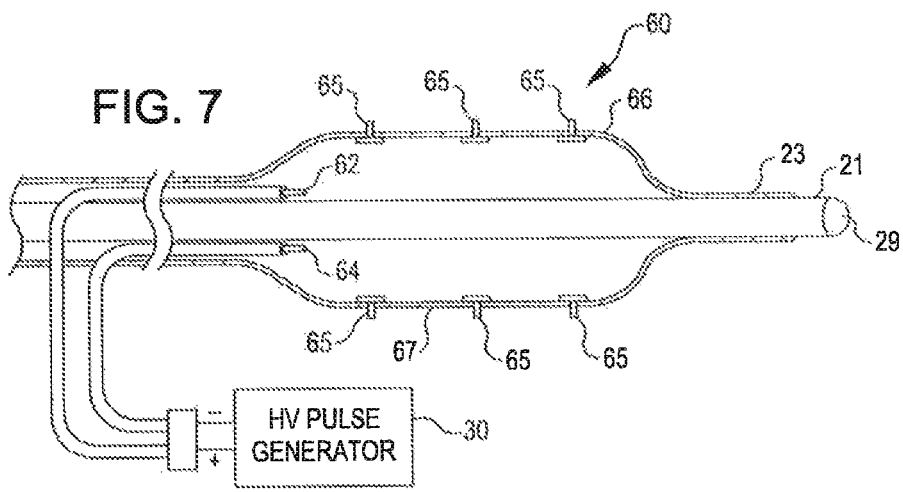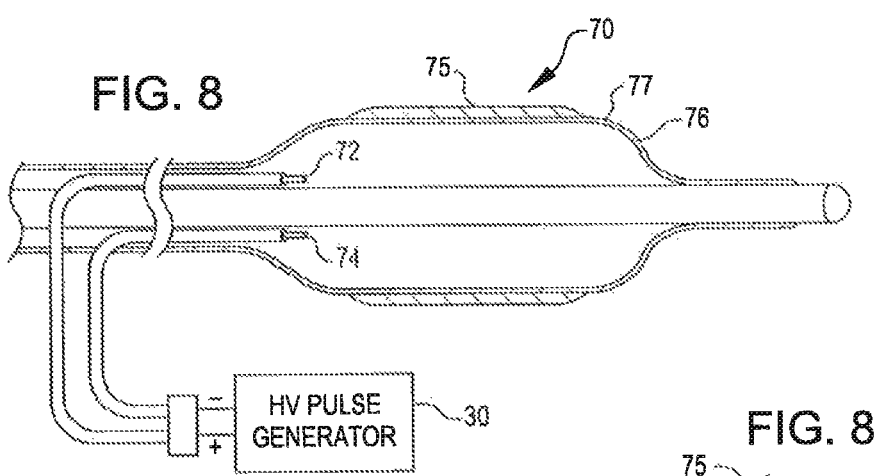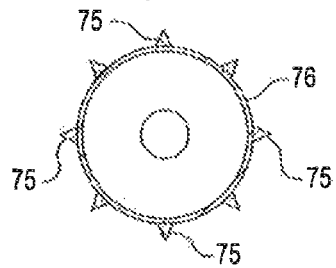

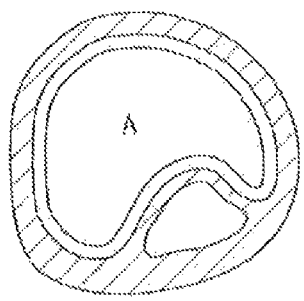
FIG. 10A
(PRIOR ART)
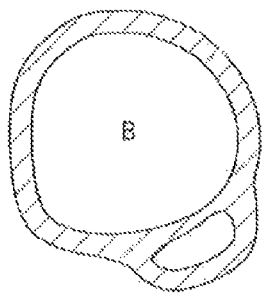
FIG. 10B
(PRIOR ART)
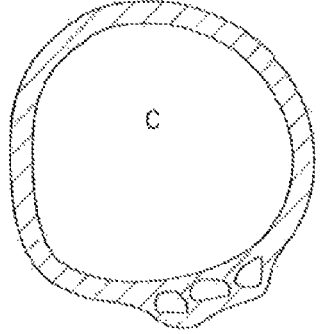
FIG. 10C
(PRIOR ART)
FIG. 11
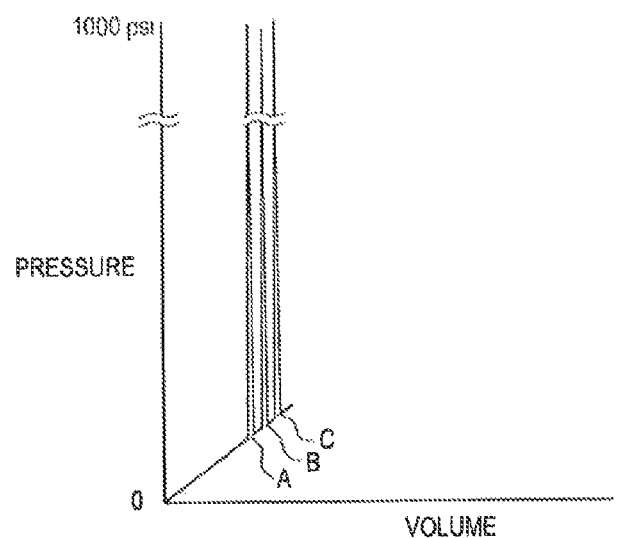
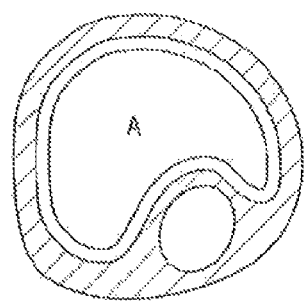
FIG. 11A
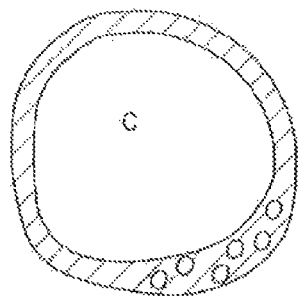
FIG. 11B FIG. 15
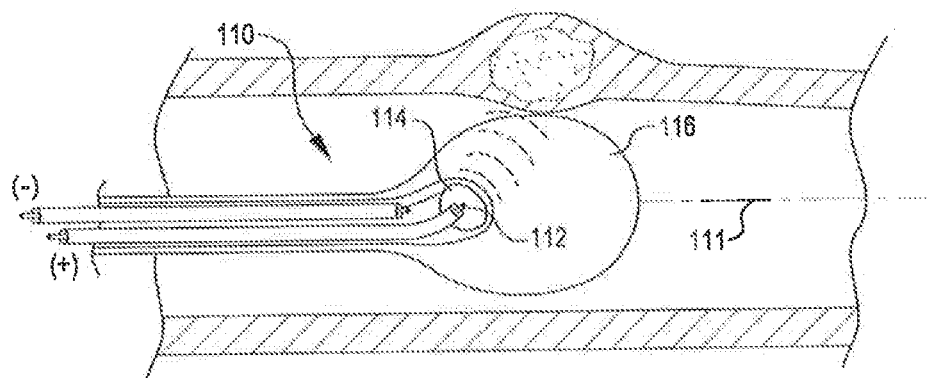
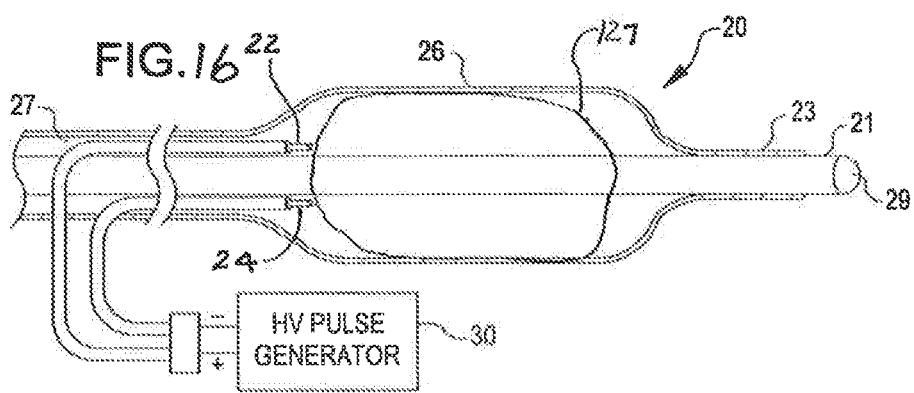
FIG. 16

NON-CAVITATION SHOCKWAVE BALLOON CATHETER SYSTEM

CROSS-REFERENCE TO RELATED APPLICATION

This application is a continuation-in-part of U.S. application Ser. No. 12/482,995 filed on Jun. 11, 2009 (pending), which application claims the benefit of priority to U.S. Provisional Application No. 60/061,170 filed on Jun. 13, 2008, all of which applications are incorporated herein by reference in their entireties for all purposes.

BACKGROUND OF THE INVENTION

The present invention relates to a treatment system for percutaneous coronary angioplasty or peripheral angioplasty in which a dilation catheter is used to cross a lesion in order to dilate the lesion and restore normal blood flow in the artery. It is particularly useful when the lesion is a calcified lesion in the wall of the artery. Calcified lesions require high pressures (sometimes as high as 10-15 or even 30 atmospheres) to break the calcified plaque and push it back into the vessel wall. With such pressures comes trauma to the vessel wall which can contribute to vessel rebound, dissection, thrombus formation, and a high level of restenosis. Non-concentric calcified lesions can result in undue stress to the free wall of the vessel when exposed to high pressures. An angioplasty balloon when inflated to high pressures can have a specific maximum diameter to which it will expand but the opening in the vessel under a concentric lesion will typically be much smaller. As the pressure is increased to open the passage way for blood the balloon will be confined to the size of the opening in the calcified lesion (before it is broken open). As the pressure builds a tremendous amount of energy is stored in the balloon until the calcified lesion breaks or cracks. That energy is then released and results in the rapid expansion of the balloon to its maximum dimension and may stress and injure the vessel walls.

SUMMARY OF THE INVENTION

In one embodiment, an angioplasty catheter includes an elongated carrier and an angioplasty balloon about the carrier in sealed relation thereto. The balloon is arranged to receive a fluid therein that inflates the balloon. The catheter further includes a shock wave generator within the balloon that forms a rapidly expanding and collapsing bubble within the balloon to form mechanical shock waves within the balloon which travel through the balloon to adjacent tissue.

The shock wave generator forms a first shock wave as the bubble expands and a second shock wave as the bubble collapses.

The first and second shock waves have energies and the energy of the first shock wave may be greater than the energy of the second shock wave. The shock wave generator is preferably arranged to form a bubble that is non-symmetrical in configuration or contains a structure, such as a guide wire lumen sheath, in the center line of the bubble. It is especially preferable to form bubbles that are not symmetrical about a single point. Bubbles in a balloon that are symmetrical in a tubular shape may generate a mild shockwave. However, a guidewire lumen sheath within the balloon center will prevent a tubular bubble from collapsing on itself so that the molecules do not collide with each other to create a strong second shock wave of significance.

The shock wave generator may therefor be arranged to form a bubble that is non-spherical in configuration. The shock wave generator is then arranged to suppress the second shock wave.

The shock wave generator may include an electrical arc generator. The electrical arc generator may include at least one conductive electrode. The at least one conductive electrode may be formed from stainless steel or tungsten. Alternatively, the shock wave generator may include a laser generator.

In another embodiment, a method includes the steps of providing a catheter including an elongated carrier, an angioplasty balloon about the carrier in sealed relation thereto, wherein the balloon is arranged to receive a fluid therein that inflates the balloon. The method further includes inserting the catheter into a body lumen of a patient adjacent a blockage or restriction of the body lumen, admitting fluid into the balloon, and forming a rapidly expanding and collapsing bubble within the balloon to form mechanical shock waves within the balloon.

The forming step includes creating a first shock wave as the bubble expands and creating a second shock wave as the bubble collapses. The first and second shock waves have energies, and the forming step may further include causing the energy of the first shock wave to be greater than the energy of the second shock. The forming step may further include causing the bubble to have a non-symmetrical configuration as, for example by an obstructed center line. The forming step may further include forming a bubble that is non-spherical in configuration. The method may include the further step of suppressing the second shock wave.

The forming step may include creating an electrical arc within the balloon. The forming step may alternatively include generating a laser within the balloon.

BRIEF DESCRIPTION OF THE DRAWINGS

For illustration and not limitation, some of the features of the present invention are set forth in the appended claims. The various embodiments of the invention, together with representative features and advantages thereof, may best be understood by making reference to the following description taken in conjunction with the accompanying drawings, in the several figures of which like reference numerals identify identical elements, and wherein:

FIG. 3A shows voltage pulses that may be obtained with the generator of FIG. 3.

FIG. 4 is a side view of the catheter of FIG. 2 showing an arc between the electrodes and simulations of the shock wave flow.

FIG. 5 is a side view of a dilating catheter with insulated electrodes within the balloon and displaced along the length of the balloon according to another embodiment of the invention.

FIG. 6 is a side view of a dilating catheter with insulated electrodes within the balloon displaced with a single pole in the balloon and a second being the ionic fluid inside the balloon according to a further embodiment of the invention.

FIG. 7 is a side view of a dilating catheter with insulated electrodes within the balloon and studs to reach the calcification according to a still further embodiment of the invention.

FIG. 8 is a side view of a dilating catheter with insulated electrodes within the balloon with raised ribs on the balloon according to still another embodiment of the invention.

FIG. 8A is a front view of the catheter of FIG. 8.

FIG. 10A is a sectional view of a balloon expanding freely within a vessel.

FIG. 10B is a sectional view of a balloon constrained to the point of breaking in a vessel.

FIG. 10C is a sectional view of a balloon after breaking within the vessel.

FIG. 11 is a pressure volume curve showing the various stages in the breaking of a calcified lesion with shock waves according to an embodiment of the invention.

FIG. 11A is a sectional view showing a compliant balloon within a vessel.

FIG. 11B is a sectional view showing pulverized calcification on a vessel wall.

FIG. 15 is a side view, partly cut away, of a dilating catheter with a parabolic reflector acting as one electrode and provides a focused shock wave inside a fluid filled compliant balloon.

FIG. 16 is a side view of the dilating angioplasty balloon catheter of FIG. 2 illustrating a non-spherical shape of a steam bubble formed therein according to another embodiment of the invention.

DETAILED DESCRIPTION OF THE INVENTION

Figure 1:
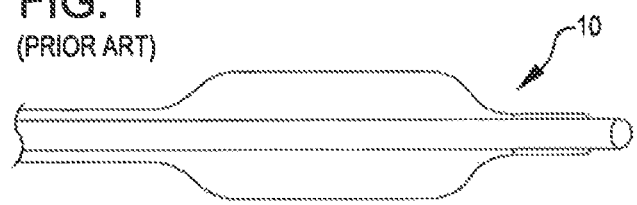
FIG. 1 is a view of the therapeutic end of a typical prior art over-the-wire angioplasty balloon catheter.

FIG. 1 is a view of the therapeutic end of a typical prior art over-the-wire angioplasty balloon catheter 10. Such catheters are usually non-complaint with a fixed maximum dimension when expanded with a fluid such as saline.

Figure 2:
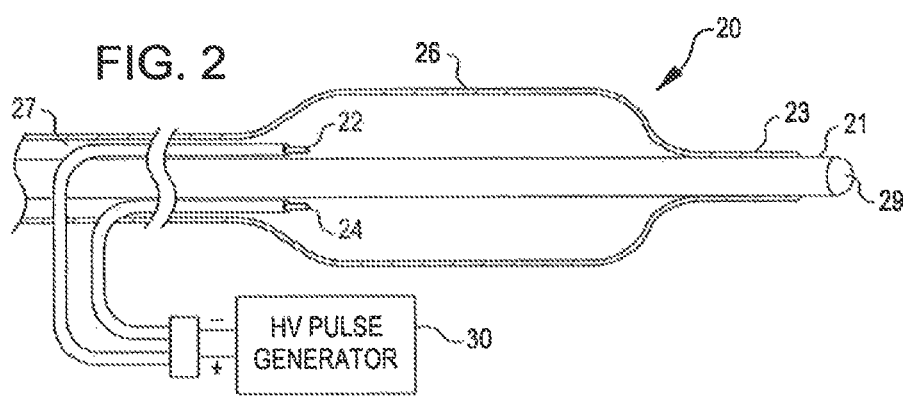
FIG. 2 is a side view of a dilating angioplasty balloon catheter with two electrodes within the balloon attached to a source of high voltage pulses according to one embodiment of the invention.

FIG. 2 is a view of a dilating angioplasty balloon catheter 20 according to an embodiment of the invention. The catheter 20 includes an elongated carrier, such as a hollow sheath 21, and a dilating balloon 26 formed about the sheath 21 in sealed relation thereto at a seal 23. The balloon 26 forms an annular channel 27 about the sheath 21 through which fluid, such as saline, may be admitted into the balloon to inflate the balloon. The channel 27 further permits the balloon 26 to be provided with two electrodes 22 and 24 within the fluid filled balloon 26. The electrodes 22 and 24 are attached to a source of high voltage pulses 30. The electrodes 22 and 24 are formed of metal, such as stainless steel or tungsten, and are placed a controlled distance apart to allow a reproducible arc for a given voltage and current. The electrical arcs between electrodes 22 and 24 in the fluid are used to generate shock waves in the fluid. The variable high voltage pulse generator 30 is used to deliver a stream of pulses to the electrodes 22 and 24 to create a stream of shock waves within the balloon 26 and within the artery being treated (not shown). The magnitude of the shock waves can be controlled by controlling the magnitude of the pulsed voltage, the current, the duration and repetition rate. The insulating nature of the balloon 26 protects the patient from electrical shocks.

The balloon 26 may be filled with water or saline in order to gently fix the balloon in the walls of the artery in the direct proximity with the calcified lesion. The fluid may also contain an x-ray contrast to permit fluoroscopic viewing of the catheter during use. The carrier 21 includes a lumen 29 through which a guidewire (not shown) may be inserted to guide the catheter into position. Once positioned the physician or operator can start with low energy shock waves and increase the energy as needed to crack the calcified plaque. Such shockwaves will be conducted through the fluid, through the balloon, through the blood and vessel wall to the calcified lesion where the energy will break the hardened plaque without the application of excessive pressure by the balloon on the walls of the artery.

Figure 3:
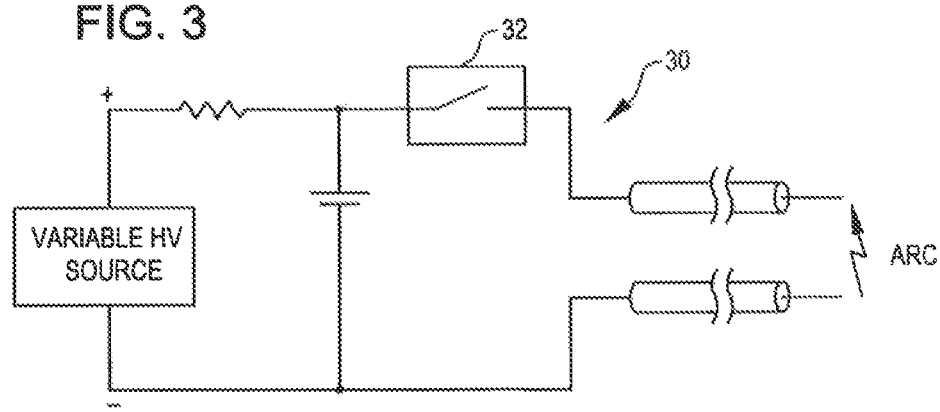
FIG. 3 is a schematic of a high voltage pulse generator.

FIG. 3 is a schematic of the high voltage pulse generator 30. FIG. 3A shows a resulting waveform. The voltage needed will depend on the gap between the electrodes and is generally 100 to 3000 volts. The high voltage switch 32 can be set to control the duration of the pulse. The pulse duration will depend on the surface area of the electrodes 22 and 24 and needs to be sufficient to generate a gas bubble at the surface of the electrode causing a plasma arc of electric current to jump the bubble and create a rapidly expanding and collapsing bubble, which creates the mechanical shock wave in the balloon. Such shock waves can be as short as a few microseconds. Since both the rapid expansion and the collapse create shockwaves, the pulse duration can be adjusted to favor one over the other. A large steam bubble will generate a stronger shockwave than a small one. However, more power is needed in the system to generate this large steam bubble. Traditional lithotripters try to generate a large steam bubble to maximize the collapsing bubble's shockwave. Within a balloon such large steam bubbles are less desirable due to the risk of balloon rupture. By adjusting the pulse width to a narrow pulse less than two microseconds or even less than one microsecond a rapidly expanding steam bubble and shockwave can be generated while at the same time the final size of the steam bubble can be minimized. The short pulse width also reduces the amount of heat in the balloon to improve tissue safety.

FIG. 4 is a cross sectional view of the shockwave catheter 20 showing an arc 25 between the electrodes 22 and 24 and simulations of the shock wave flow 28. The shock wave 28 will radiate out from the electrodes 22 and 24 in all directions and will travel through the balloon 26 to the vessel where it will break the calcified lesion into smaller pieces.

FIG. 5 shows another dilating catheter 40. It has insulated electrodes 42 and 44 within the balloon 46 displaced along the length of the balloon 46.

FIG. 6 shows a dilating catheter 50 with an insulated electrode 52 within the balloon 56. The electrode is a single electrode pole in the balloon, a second pole being the ionic fluid 54 inside the balloon. This unipolar configuration uses the ionic fluid as the other electrical pole and permits a smaller balloon and catheter design for low profile balloons. The ionic fluid is connected electrically to the HV pulse generator 30.

FIG. 7 is another dilating 60 catheter with electrodes 62 and 64 within the balloon 66 and studs 65 to reach the calcification. The studs 65 form mechanical stress risers on the balloon surface 67 and are designed to mechanically conduct the shock wave through the intimal layer of tissue of the vessel and deliver it directly to the calcified lesion.

FIG. 8 is another dilating catheter 70 with electrodes 72 and 74 within the balloon 76 and with raised ribs 75 on the surface 77 of the balloon 76. The raised ribs 75 (best seen in FIG. 8A) form stress risers that will focus the shockwave energy to linear regions of the calcified plaque.

Figure 9:
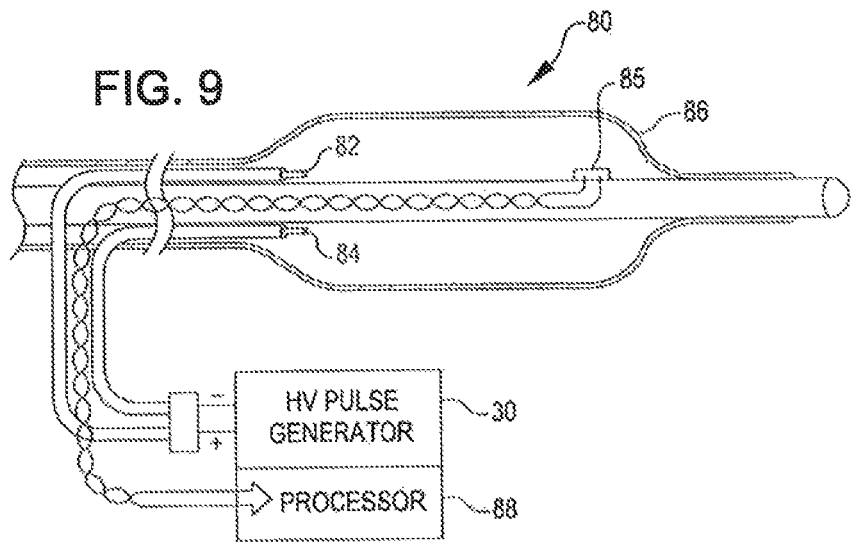
FIG. 9 is a side view of a dilating catheter with insulated electrodes within the balloon and a sensor to detect reflected signals according to a further embodiment of the invention.

FIG. 9 is a further dilating catheter 80 with electrodes 82 and 84 within the balloon 86. The catheter 80 further includes a sensor 85 to detect reflected signals. Reflected signals from the calcified plaque can be processed by a processor 88 to determine quality of the calcification and quality of pulverization of the lesion.

Figure 10:
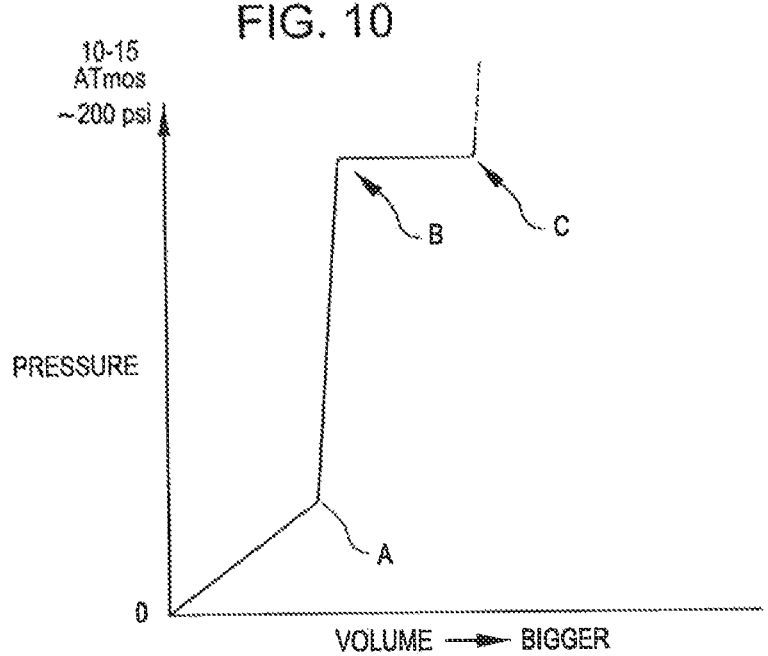
FIG. 10 is a pressure volume curve of a prior art balloon breaking a calcified lesion.

FIG. 10 is a pressure volume curve of a prior art balloon breaking a calcified lesion. FIG. 10B shows the build up of energy within the balloon (region A to B) and FIG. 10C shows the release of the energy (region B to C) when the calcification breaks. At region C the artery is expanded to the maximum dimension of the balloon. Such a dimension can lead to injury to the vessel walls. FIG. 10A shows the initial inflation of the balloon.

FIG. 11 is a pressure volume curve showing the various stages in the breaking of a calcified lesion with shock waves according to the embodiment. The balloon is expanded with a saline fluid and can be expanded to fit snugly to the vessel wall (Region A) (FIG. 11A) but this is not a requirement. As the High Voltage pulses generate shock waves (Region B and C) extremely high pressures, extremely short in duration will chip away the calcified lesion slowly and controllably expanding the opening in the vessel to allow blood to flow un-obstructed (FIG. 11B).

Figure 12:
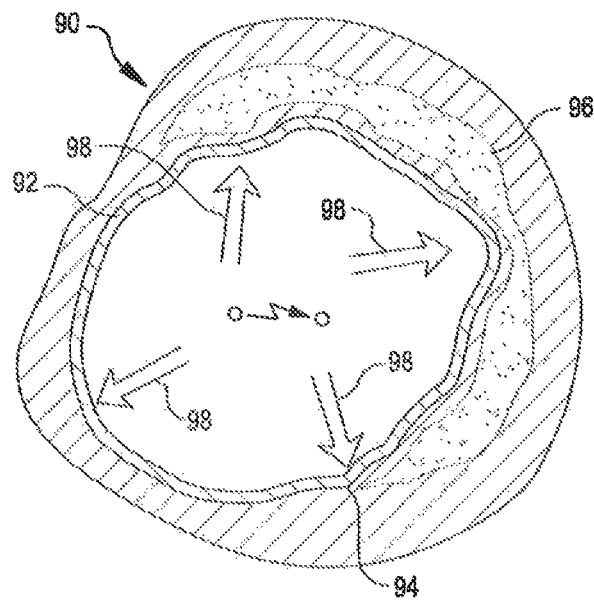
FIG. 12 illustrates shock waves delivered through the balloon wall and endothelium to a calcified lesion.

FIG. 12 shows, in a cutaway view, shock waves 98 delivered in all directions through the wall 92 of a saline filled balloon 90 and intima 94 to a calcified lesion 96. The shock waves 98 pulverize the lesion 96. The balloon wall 92 may be formed of non-compliant or compliant material to contact the intima 94.

Figure 13:
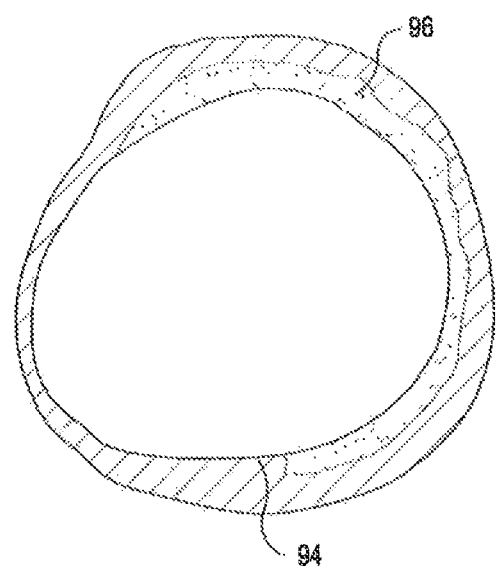
FIG. 13 shows calcified plaque pulverized and smooth a endothelium restored by the expanded balloon after pulverization.

FIG. 13 shows calcified plaque 96 pulverized by the shock waves. The intima 94 is smoothed and restored after the expanded balloon (not shown) has pulverized and reshaped the plaque into the vessel wall.

Figure 14:
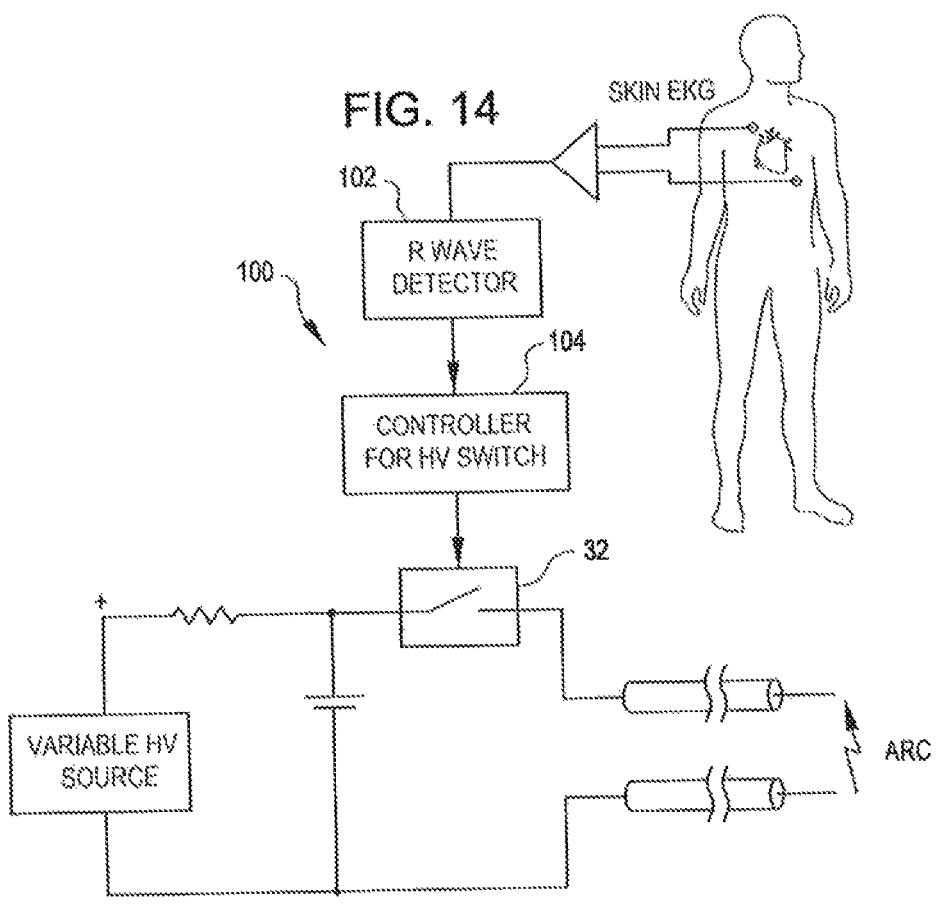
FIG. 14 is a schematic of a circuit that uses a surface EKG to synchronize the shock wave to the "R" wave for treating vessels near the heart.

FIG. 14 is a schematic of a circuit 100 that uses the generator circuit 30 of FIG. 3 and a surface EKG 102 to synchronize the shock wave to the "R" wave for treating vessels near the heart. The circuit 100 includes an R-wave detector 102 and a controller 104 to control the high voltage switch 32. Mechanical shocks can stimulate heart muscle and could lead to an arrhythmia. While it is unlikely that shockwaves of such short duration as contemplated herein would stimulate the heart, by synchronizing the pulses (or bursts of pulses) with the R-wave, an additional degree of safety is provided when used on vessels of the heart or near the heart. While the balloon in the current drawings will provide an electrical isolation of the patient from the current, a device could be made in a non-balloon or non-isolated manner using blood as the fluid. In such a device, synchronization to the R-wave would significantly improve the safety against unwanted arrhythmias.

FIG. 15 shows a still further dilation catheter 110 wherein a shock wave is focused with a parabolic reflector 114 acting as one electrode inside a fluid filled compliant balloon 116. The other electrode 112 is located at the coaxial center of the reflector 114. By using the reflector as one electrode, the shock wave can be focused and therefore pointed at an angle (45 degrees, for example) off the center line 111 of the catheter artery. In this configuration, the other electrode 112 will be designed to be at the coaxial center of the reflector and designed to arc to the reflector 114 through the fluid. The catheter or electrode and reflector can be rotated if needed to break hard plaque as it rotates and delivers shockwaves.

As previously mentioned in connection with FIGS. 3 and 3A, producing a shock wave with an electrical arc requires a combination of voltage, electrode spacing, electrode surface area, and pulse duration. The voltage needed to produce an electrical arc between the electrodes will depend on the gap between the electrodes, but will generally be between 100 and 3000 volts. The pulse duration may be 10 microseconds or less but will depend on the surface area of the electrodes. For example, the spacing between electrodes 22 and 24 may be between 0.002 to 0.020 inches. The surface area of the negative electrode may be that of the end surface of a 0.010 inch diameter (or less) conductor, such as stainless steel. The surface area of the positive electrode may be 5 times the negative electrode surface area. The resulting gas bubble and high voltage causes a plasma arc of electric current to jump the bubble. The heat of the arc creates a rapidly expanding and collapsing steam bubble.

The rapidly expanding and collapsing steam bubble can generate first and second shockwaves, respectively, under certain conditions. The first shockwave can be generated if the rapid expansion of the bubble is very fast. The bubble expansion must be rapid enough to create a compression pressure pulse of a few Mega Pascals, for example, five Mega Pascals, lasting less than 1 to 2 microseconds. The sudden rise in pressure of more than 5 Mega Pascal in less than 2 microseconds will result in a propagating shockwave that moves in water at a speed of 1500 meters/second. The second shockwave is generated after a cooling off period when the bubble collapses. If the bubble is symmetrical or spherical, the sonic output of the collapsing bubble will be generally very large because it will collapse in a symmetrical manner focusing its energy down to a coherent point. This collapse occurs a delay time after the initial electrical plasma when the steam bubble collapses because of cooling. When the steam forming the bubble cools and condenses back to water, the bubble suddenly becomes a cavitation bubble and begins to collapse rapidly. Depending on the initial bubble size and temperature this delay may be as short as 100 microseconds or as long as 4 milliseconds after the plasma arc.

When a steam bubble is formed within an angioplasty balloon during and following a plasma arc, it is confined to the space available inside the angioplasty balloon. For a 4 mm diameter balloon with a guide wire lumen as, for example angioplasty balloon 26 of FIG. 16, a steam bubble 127, bigger than about 1.6 mm diameter, will be constrained to be non-spherical. As may be noticed in FIG. 16, steam bubble 127 is confined by the balloon 26 and is essentially elliptically shaped. Because the bubble 127 is non-symmetrical or non-spherical, it will be less effective at generating the second shock wave upon collapse. For a 5 mm diameter balloon, the maximum spherical bubble size would be about 2.1 mm diameter.

The shockwave energy produced from the collapse of such steam bubbles is highest if they remain spherical. When the walls of the angioplasty balloon distort the bubble shape to a non-spherical shape, the shockwave generated from the bubble collapse will be severely attenuated. In addition, a stenosis of undetermined shape will also have an effect on balloon shape to further reduce the maximum size of a yet still spherical bubble. Tiny spherical bubbles, such as those with diameters between about 1.6 to 2.1 millimeters, generate much smaller shockwaves. In fact, in some cases, a stenosis may reduce the balloon diameter to nearly the diameter of the guide wire sheath 21, thus, not even allowing bubbles having a diameter as big as 1.6 millimeters to form. It is clear that the second shock wave resulting from a cavitation bubble collapse cannot be relied upon to generate a shockwave strong enough to break the calcium.

In view of the above, the stenosis or calcium breaking energy must come from the first shock wave created by the rapidly expanding bubble where bubble shape is not important to shock wave generation and not from the collapse of a cavitation bubble. By arranging the shock wave generator within the catheter balloon to create a steam bubble with a rapid rise time (less than 1 to 2 microseconds), the first (non-cavitation) shock wave resulting from bubble expansion will be large while the second (cavitation) shock wave resulting from the bubble being forced to assume a non-spherical or non-symmetrical shape to collapse in a non-uniform manner will be small or suppressed. The expanding bubble shockwave will be large and the collapsing bubble shock wave will be small due to the bubble shape being distorted by the non-spherical shape of the balloon wall and the guide wire sheath. This results in the generation of a large, non-cavitation, expanding bubble shock wave and in a weak, cavitation, collapsing bubble shock wave. The collapse of a non-symmetrical bubble results in formation of water jets inside the balloon which help circulate the fluids and cool the balloon, releasing some of the heat from the energy delivered to it.

The system may be further improved by reducing the final size of the stream bubble by limiting the pulse duration of the plasma arc to less than one or two microseconds. This will minimize the final size of the steam bubble to lower the stress on the balloon structure and lower the latent heat produced inside the balloon per shock. A system that relies on the rapid expansion generating the shockwave and not on the rapid collapse can therefore operate with lower balloon stress and lower latent heat generation.

The sonic output of the expanding steam bubble depends upon a rapid expansion of the bubble during formation. If the voltage and current are applied with a slow rise time or if the maximum current is limited, the expansion of the plasma induced steam bubble will be too slow to generate a shockwave. If the voltage and current rise times in the plasma of the arc are less than 2 microseconds or even 1 microsecond, a rapidly expanding bubble will form an effective shockwave. The shockwave formation upon rapid expansion of the bubble is independent on bubble shape in the balloon and independent of the size of a restricted area in the balloon caused by a stenosis. The shockwave formed is dependent upon the rapid formation of a plasma arc and is controlled by electrical parameters such as voltage and current rise times being less than 1-2 microseconds. Thus the rapidly expanding bubble is the most reliable shockwave generation source in an angioplasty balloon and leads to the least balloon stress and lowest heat generation.

Figure 17:
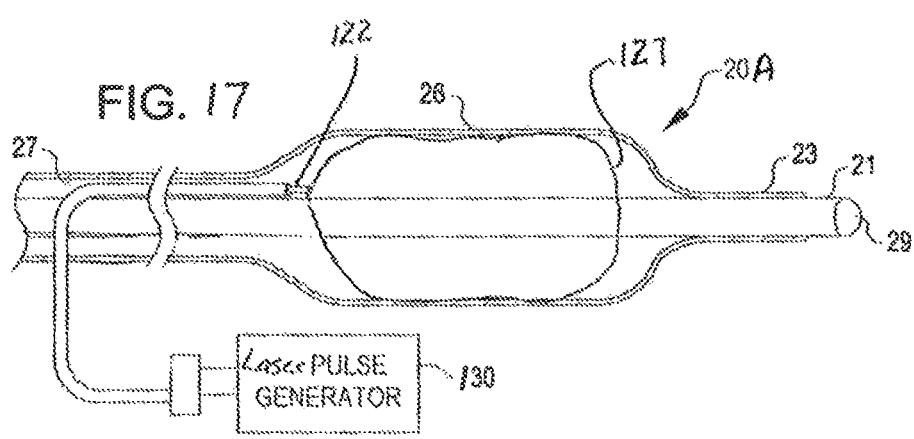
FIG. 17 is a side view of another dilating angioplasty balloon catheter having a shock wave generator therein formed by a laser source according to a still further embodiment of the invention.

FIG. 17 shows another angioplasty balloon catheter 20A according to another aspect of the invention. The catheter uses the same balloon 26 as shown in FIG. 2. Here however, a laser fiber 122 connected to a laser pulse generator 130 is delivered into the balloon interior between the guide wire sheath and the balloon wall. The laser pulse generator 130 and the laser fiber 122 may also be used to create a shockwave by means of generating a steam bubble as well. In a similar manner as described previously with respect to electrical arc shock wave generators, the laser generated bubble 127 can produce shockwaves during the rapid expansion and collapse of the steam bubble. By generating bubbles rapidly, the laser may also be used to create shockwaves on the rapid expansion phase which become distorted by the structures inside the balloon and produce weak shockwaves upon collapse.

As may be seen from the forgoing, the sonic output of a non-spherical or non-symmetrical cavitation bubble collapsing may be very small and ineffective. Inside an angioplasty balloon the limited space available will not allow a steam bubble to be very large before it becomes distorted from an ideal spherical shape. Also, the variable size of an arterial restriction intended to be treated with the angioplasty balloon will further distort the shape of the collapsing cavitation bubble. The size of a bubble generated in a balloon depends on the energy applied to it and the pressure in the balloon. The bubble size (volume) is therefore difficult to control and its spherical shape is not controllable inside the working angioplasty balloon. Thus the sonic output (shockwave) caused by the collapse of the cavitation bubble in this application is not reliable while the sonic output of the expanding bubble is reliable and may be relied upon for arterial stenosis treatment.

While particular embodiments of the present invention have been shown and described, modifications may be made. For example, it is therefore intended in the appended claims to cover all such changes and modifications which fall within the true spirit and scope of the invention as defined by those claims.

What is claimed is:

1. An angioplasty catheter comprising:
    an elongated carrier;
    an angioplasty balloon about the carrier in sealed relation thereto, the balloon being arranged to receive a fluid therein that inflates the balloon wherein the balloon includes a central portion that extends longitudinally along the carrier, said central portion having a constant diameter; and
    a shock wave generator located within the balloon and aligned with the central portion thereof for generating a plasma arc within the balloon that in turn forms a rapidly expanding and collapsing bubble within the balloon and wherein the expansion of the bubble creates a first shock wave and the collapse of the bubble creates a second shock wave and wherein the bubble is non-spherical and wherein the plasma arc is limited to be shorter than two microseconds whereby the energy in the first shock wave is greater than the energy in the second shock wave.

2. The catheter of claim 1, wherein the shock wave generator comprises an electrical arc generator.

3. The catheter of claim 2, wherein the electrical arc generator is arranged to form a plasma arc having a duration of less than about one microsecond.

4. The catheter of claim 2, wherein the electrical arc generator is rotatable.

5. The catheter of claim 4, wherein the electrical arc generator comprises at least one conductive electrode.

6. The catheter of claim 5, wherein the at least one conductive electrode is formed from stainless steel.

7. The catheter of claim 5, wherein the at least one conductive electrode is formed from tungsten.

8. A method comprising:
    providing a catheter including an elongated carrier, an angioplasty balloon about the carrier in sealed relation thereto, the balloon being arranged to receive a fluid therein that inflates the balloon wherein the balloon includes a central portion that extends longitudinally along the carrier, said central portion having a constant diameter;
    inserting the catheter into a body lumen of a patient adjacent a blockage or restriction of the body lumen;
    admitting fluid into the balloon; and generating a plasma arc within the balloon aligned with the central portion of the balloon, said plasma arc is limited to being shorter than two microseconds, said plasma are forming a rapidly expanding and collapsing bubble within the balloon and wherein the expansion of the bubble creates a first shock wave and the collapse of the bubble creates a second shock wave and wherein the bubble is non-spherical whereby the energy in the first shock wave is greater than the energy in the second shock wave.

9. The method of claim 8, wherein the duration of the plasma arc is less than one microsecond.

10. A catheter system comprising:
an elongated carrier;
a balloon about the carrier in sealed relation thereto, the balloon being arranged to receive a fluid therein that inflates the balloon wherein the balloon includes a central portion that extends longitudinally along the carrier, said central portion having a constant diameter;
a shock wave generator within the balloon and aligned with the central portion thereof, said shock wave generator being responsive to applied voltage pulses to create a rapidly expanding and collapsing bubble within the balloon and wherein the expansion of the bubble creates a first shock wave and the collapse of the bubble creates a second shock wave and wherein the bubble is non-spherical; and
a source of voltage coupled to the shock wave generator that provides the shock wave generator with the applied voltage pulses, the applied voltage pulses including pulses formed by a capacitor discharge and wherein pulses are truncated so that an electric arc created in the balloon is shorter that two microseconds whereby the energy in the first shock wave is greater than the energy in the second shock wave.

11. The system of claim 10, wherein the pulses formed by a truncated capacitor discharge have an initial voltage amplitude of between 100 and 3,000 volts.

12. The system of claim 10, wherein the pulses are truncated so that the electric arc created in the balloon is less than one microsecond.

13. The system of claim 10, wherein the balloon is an angioplasty balloon.

14. The system of claim 10, wherein the shock wave generator comprises at least a pair of electrodes across which the voltage pulses are applied.

15. An angioplasty catheter comprising:
an elongated carrier;
an angioplasty balloon about the carrier in sealed relation thereto, the balloon being arranged to receive a fluid therein that inflates the balloon wherein the balloon includes a central portion that extends longitudinally along the carrier, said central portion having a constant diameter; and
an arc generator including a pair of electrodes positioned within a balloon and aligned with the central portion thereof and in non-touching relationship therewith, said arc generator generating a high voltage pulse sufficient to create a plasma arc between the electrodes, wherein the high voltage pulse is truncated to limit the plasma arc to be shorter than two microseconds and wherein the plasma arc forms a rapidly expanding and collapsing bubble within the balloon and wherein the expansion of the bubble creates a first shock wave and the collapse of the bubble creates a second shock wave and wherein the bubble is non-spherical whereby the energy in the first shock wave is greater than the energy in the second shock wave.

16. The catheter of claim 15, the plasma arc is limited to be shorter than about one microsecond.

17. The system of claim 15 wherein the high voltage pulse is formed from a capacitive discharge and wherein the discharge is truncated to control the duration of the plasma arc.

* * * * *